United States Patent [19]

Fischer et al.

[11] 4,005,147

[45] Jan. 25, 1977

[54] PRODUCTION OF α,β-UNSATURATED KETONES

[75] Inventors: Roman Fischer, Ludwigshafen; Norbert Goetz, Bobenheim-Roxheim; Herbert Mueller, Frankenthal, all of Germany

[73] Assignee: Badische Anilin- & Soda-Fabrik Aktiengesellschaft, Ludwigshafen (Rhine), Germany

[22] Filed: Oct. 10, 1972

[21] Appl. No.: 295,959

[30] Foreign Application Priority Data

Oct. 13, 1971 Germany .................. 2150992

[52] U.S. Cl. ............ 260/593 R; 260/586 C; 260/590 R
[51] Int. Cl.² .......................... C07C 45/00
[58] Field of Search ........ 260/593 R, 593 A, 593 F

[56] References Cited

FOREIGN PATENTS OR APPLICATIONS 1,203,243  10/1965  Germany .................. 260/593
1,010,695  11/1962  United Kingdom ......... 260/593 R Primary Examiner—James O. Thomas, Jr.
Assistant Examiner—James H. Reamer
Attorney, Agent, or Firm—Johnston, Keil, Thompson & Shurtleff

[57] ABSTRACT

A process for the production of α,β-unsaturated ketones by reaction of an aldehyde with a ketone in the presence of a catalyst consisting essentially of zinc oxide in the liquid phase. The ketones obtained are suitable in some cases as solvents and in some cases as intermediates for the production of valuable odorants, dyes, plastics and especially natural substances.

9 Claims, No Drawings

PRODUCTION OF α,β-UNSATURATED KETONES

The invention relates to a process for the production of ketones unsaturated in the α,β-position to the carbonyl group by reacting in the liquid phase an aldehyde with a ketone in the presence of a catalyst consisting essentially of zinc oxide.

Houben-Weyl, "Methoden der organischen Chemie," volume 7/1, pages 77 et seq. and "Organic Reactions," volume 16, pages 27 to 47, 69 to 78 and 177 et seq. disclose the fact that aldehydes and ketones can be converted to α,β-unsaturated ketones. Temperatures of from 5° to 25° C are preferred for this aldol condensation ("Organic Reactions," loc.cit., page 77). The numerous catalysts used in these methods, for example alkali and alkaline earth metal hydroxides, organic bases, alkali metal salts and alcoholates promote autocondensation of the aldehydes and ketones and therefore cause the formation of large amounts of by-products in most cases. The processing of such mixtures involves high expenditure because the catalyst used has to be removed or neutralized prior to the processing. The yields of end product are often unsatisfactory.

It is furthermore known from U.S. Pat. No. 2,549,508 that aldehydes and ketones can be converted into unsaturated ketones of high molecular weight in the gas phase at temperatures of from 500° to 1000° C in the presence of a catalyst consisting essentially of zinc oxide and from 1 to 15% by weight of zirconium oxide. In this process however only low conversions and low yields are achieved. Moreover high expenditure for equipment is required for reactions in the presence of hydrogen at the said temperatures for safety reasons. Moreover cracking processes take place at the surface of the catalyst in such reactions and these have a negative effect on the life of the catalyst.

The reaction of two identical or different aldehydes or ketones in the liquid phase at elevated temperature and in the presence of a catalyst (obtained by calcining a mixture of molybdenum oxide, magnesium oxide with or without zinc oxide or compounds of these metals) to from α,β-unsaturated aldehydes or ketones is known from German Pat. No. 1,203,243.

According to the method described in the said patent good conversions and very good yields of α,β-unsaturated aldehydes are obtained in the condensation of aldehydes with one another, particularly in the condensation of n-butyraldehyde to 2-ethylhexenal.

The process of German Pat. No. 1,203,243 is not so suitable for the reaction of aldehydes with ketones to form α,β-unsaturated ketones, considerably lower conversions and selectivities being achieved. This is particularly noticeable when not only isobutyraldehyde (i.e., an aldehyde which does not undergo autocondensation) is reacted with a ketone by the method of the said German patent, but also aldehydes are used which readily undergo autocondensation, as for example 3,3-dimethylacrolein and citral (see Comparative Experiment: Example 23).

It is therefore the object of the invention to develop a process which enables aldehydes, particularly aldehydes having a tendency for autocondensation, to be reacted selectively with ketones to α,β-unsaturated ketones with good conversions and very good yields.

We have found that α,β-unsaturated ketones of the general formula (I):

in which $R^1$ and $R^2$ are branched or linear, saturated or unsaturated, aliphatic or cycloaliphatic-aliphatic hydrocarbon radicals of one to 20, particularly one to 16, carbon atoms or saturated or unsaturated cycloaliphatic hydrocarbon radicals of five to 12 carbon atoms, which may contain alkyl groups as substituents and/or endoalkylene groups or may be an araliphatic hydrocarbon radical of seven to 15 carbon atoms, preferably benzyl, or an aromatic hydrocarbon radical, preferably phenyl, $R^3$ is hydrogen or an aliphatic hydrocarbon radical of one to 10 carbon atoms and moreover $R^1$ and $R^3$ together with the two adjacent carbon atoms may be members of a common alicyclic ring, can be prepared by reaction of an aldehyde of the general formla (II):

in which $R^2$ has the meanings given above with a ketone of the general formula (III):

in which $R^1$ and $R^3$ have the meanings given above, in liquid phase, in excellent yields and with good conversions by carrying out the reaction in the presence of a catalyst consisting essentially of zinc oxide.

This result is particularly surprising because on the basis of the comparison of catalysts in the condensation of n-butyraldehyde to 2-ethylhexenal the conclusion is drawn in German Pat. No. 1,203,243 that zinc oxide alone or combined with only one other oxide constituent gives poorer conversions and selectivities than the catalyst consisting of three components. It is also surprising that the catalytic reaction in liquid phase proceeds so advantageously for unsaturated and sensitive aldehydes and ketones.

Suitable aldehydes are those of the formula (II) in which $R^2$ is a branched or unbranched, saturated or unsaturated, aliphatic or cycloaliphatic or cycloaliphatic-aliphatic hydrocarbon radical or one to 20, preferably one to 16 carbon atoms or a saturated or unsaturated cycloaliphatic hydrocarbon radical of five to 12 carbon atoms which may also contain alkyl groups as substituents and/or an endoalkylene group, or an araliphatic hydrocarbon radical of seven to 15 carbon atoms, particularly or an aromatic hydrocarbon radical, preferably phenyl.

The process according to the invention is of special advantage for the reaction of an aldehyde readily undergoing autocondensation with a ketone because the process of German Pat. No. 1,203,243 and the prior art condensation methods carried out in the presence of alkaline condensing agents are not very advantageous.

Examples of aldehydes which readily undergo autocondensation are aldehydes of the general formula (IIa):

where the radical $R^{2a}$ generally has the meanings given above for $R^2$ but contains one carbon atom less in each case than the corresponding radical $R^2$. Preferred aldehydes of the formula (IIa) are those in which the radical $R^{2a}$ is a branched or linear, saturated or unsaturated aliphatic hydrocarbon radical of one to 15 carbon atoms which may bear alkyl groups as substituents, or an araliphatic group of seven to 10 carbon atoms.

Aldehydes which readily undergo autocondensation also include aldehydes of the general formula (IIb):

where the radical $R^{2b}$ generally has the meanings given above for $R^2$ but contains two to four carbon atoms than the corresponding radical $R^2$. The radical $R^{2c}$ in formula (IIb) is generally methyl or ethyl. Preferred aldehydes of the formula (IIb) are those in which $R^{2b}$ is a branched or linear, saturated or unsaturated, aliphatic hydrocarbon radical or one to 12 carbon atoms. The reaction of aldehydes of formula (IIb) with ketones is of particular industrial significance because in this reaction $\alpha,\beta,\gamma,\delta$-unsaturated ketones are formed some of which play an important part in terpene chemistry and could only be prepared hitherto by a troublesome method. The reactions of such alkali-sensitive and temperature-sensitive aldehydes as 3,3-dimethylacrolein, citral and farnesal wit acetone to form 2-methyl-2,4-heptadien-6-one, pseudoionone and farnesalacetone may be emphasized in particular.

The aldehydes hereinafter specified are examples of those which are suitable for the reaction according to the invention:

acetaldehyde, propionaldehyde, n-butyraldehyde, isobutyraldehyde, tert-butyraldehyde, crotonaldehyde, tiglaldehyde, 3,3-dimethylacrolein, enanthaldehyde, citral, $\alpha$-cyclocitrial, $\beta$-cyclocitral, benzaldehyde, cinnamaldehyde, phenylacetaldehyde, hydrocinnamaldehyde, 2-phenylpropionaldehyde, cyclohexylaldehyde, n-valeraldehyde, isovaleraldehyde, anisaldehyde, n-heptaldehyde, farnesal, phytal and vitamin a aldehyde.

Suitable ketones include ketones of the formula (III) in which $R^1$ is a branched or linear, saturated or unsaturated, aliphatic or cycloaliphatic-aliphatic hydrocarbon radical of one to 20, preferably one to 16 carbon atoms or a saturated or unsaturated cycloaliphatic hydrocarbon radical of five to 12 carbon atoms which may bear alkyl groups as substituents and/or may contain an endoalkylene group or an araliphatic hydrocarbon radical of seven to 15 carbon atoms, preferably a benzyl group, or an aromatic hydrocarbon radical, preferably a phenyl group, $R^3$ is hydrogen or an aliphatic hydrocarbon radical of one to 10 carbon atoms, preferably hydrogen, and moreover $R^1$ and $R^3$ together with the two adjacent carbon atoms may be members of a common alicyclic ring.

When a ketone which has both a methylene group annd a methyl group in the $\alpha$-position to the keto group, for example methyl ethyl ketone, is used, the reaction takes place predominantly on the methyl group in contrast to prior art condensation methods.

The best yields are obtained when cycloalkanones or ketones which bear a methyl group in the $\alpha$-position to the carbonyl group are used, i.e., ketones in which $R^3$ is hydrogen or $R^1$ and $R^3$ together with the two adjacent carbon atoms are members of a common alicyclic ring.

Reaction with unsaturated ketones is again of particular industrial interest because their condenstion products with aldehydes play a significant role in the perfume industry.

$\alpha,\beta$-unsaturated ketones may be particularly emphasized, i.e., ketones of formula (IIIa):

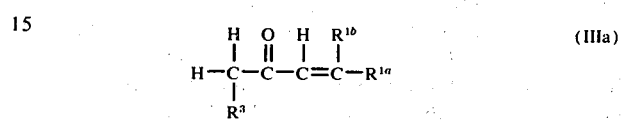

in which $R^3$ has the meanings given above, $R^{1a}$ is a branched or linear, saturated or unsaturated, aliphatic or cycloaliphatic-aliphatic hydrocarbon radical of one to 18, preferably one to 14, carbon atoms or a saturated or unsaturated cycloaliphatic hydrocarbon radical of five to 10 carbon atoms which may contain alkyl groups as substituents and $R^{1b}$ is hydrogen or alkyl of one to 4 carbon atoms. This means that $\alpha,\beta$-unsaturated ketones prepared according to the invention may be brought to reaction again.

Examples of suitable ketones of formula (III) are: acetone, methyl ethyl ketone, methyl n-propyl ketone, methyl isopropyl ketone, methyl n-butyl ketone, methyl isobutyl ketone, methyl tert-butyl ktone diethyl ketone, diacetyl, 2-methyl-2-hepten-6-one, acetophenone, cyclohexanone, cyclohexyl ethyl ketone, benzyl methyl ketone, methyl propenyl ketone, ethyl propenyl ketone, mesityl oxide, propyl propenyl ketone, isobutylideneacetone, 2-methyl-2,4-heptadien-6-one, $\beta$-ionone, farnesylacetone and geranylacetone.

A catalyst consisting essentially of zinc oxide for the process of this invention is defined as a catalyst which consists to the extent of at least 80% and preferably practically 100% of zinc oxide. It may contain small amounts, i.e., from 0 to 20%, of metal oxides or inert fillers which do not cause any other reactions of the starting materials under the reaction conditions. As far as possible however it should not contain any appreciable amount of a metal oxide which will accelerate aldehyde autocondensation, such as $Al_2O_3$, $Fe_2O_3$, $PtO_2$, $MoO_3$, or $MgO$.

The catalyst should also not contain any appreciable amounts of acid components such as $Cr_2O_3$, $Sb_2O_3$ or $Bi_2O_3$ because otherwise cyclization reactions often occur in the reaction of unsaturated starting materials.

It is of particular advantage to use practically pure zinc oxide in the form of tablets or extrudate having a diameter of about 4 to 5 mm such are used as catalyst in industry, for example in the dehydrogenation of cyclohexanol to cyclohexanone. Naturally the zinc oxide catalyst may be applied to a carrier material which is inert under the reaction conditions such as pumice, dead-burnt aluminas or carbon.

In order to carry out the process, a mixture of the starting materials and catalyst, with or without a solvent, is kept for the duration of the reaction at the reaction temperature and any pressure used. Then the end product is separated from the reaction mixture by a conventional method, for example by fractional distillation. The reaction may be carried out batchwise or continuously. In the batch method it is convenient to use an agitated autoclave. The continuous method may be carried out in a reactor or a cascade of reactors or stirred vessels for example by passing the liquid starting mixture at the reaction temperature and at atmospheric or superatmospheric pressure through a bed of catalyst.

The starting materials may be reacted in stoichiometric amounts. It is often advantageous however to use the cheaper and more stable component (the ketone) in an excess of about 0.5 to 6 moles, preferably 1 to 4 moles, per mole of aldehyde.

When stable ketones such as acetone, methyl ethyl ketone and mesityl oxide are used, it is advantageous to use from three to six times the stoichiometric amount, i.e., an excess of ketone is used as solvent. In the condensation of less stable ketones however it is advantageous to use only a stoichiometric to twice the stoichiometric amount of ketone and an inert solvent.

To concentration of the catalyst may vary within wide limits. High conversions and yields may be achieved in the batch mmethod with amounts of only 1 to 60%, preferably 5 to 50% by weight based on the amount of aldehyde. The catalyst concentration may however be considerably higher in the continuous method. The amount of aldehyde in this case is generally from 1 to 100%, preferably from 5 to 60%, by weight based on the amount of catalyst. In continuous operation from 0.1 to 10 liters of reaction mixture is generally passed over the catalyst per hour per liter of catalyst. The catalyst may usually be employed for up to one year without regeneration.

The reaction is generally carried out at a temperature of from 30° to 240° C, preferably at a temperature of from 135° to 205° C. Temperatures above 205° C are generally only necessary when starting from ketones which do not have any methyl groups in the α-position to the carbonyl group. The process may be carried out at atmospheric or superatmospheric pressure, preferably at pressures of from 20 to 100 atmospheres. The pressure and temperature are chosen so that the reaction mixture is liquid.

The reaction period of such reactions is from 5 minutes to 20 hours, preferably from 30 minutes to 10 hours, depending on the reaction temperature and the reactivity of the starting compounds.

The reaction may be carried out in the absence of solvents or in the presence of a solvent which is inert under the reaction conditions. Dialkyl ethers such as di-n-butyl ether, aliphatic hydrocarbons such as ligroin, or aromatic hydrocarbons such as toluene or xylene may be used as solvents. The solvent is used in an amount which is about twice to five times by weight the sum of the weights of the starting components.

Since the compounds formed are sensitivve to air it has proved to be advantageous to carry out the reaction while excluding air, for example under an atmosphere of nitrogen or argon.

It is possible by means of the process of the invention to prepare in a simple manner with good conversions and in excellent yields a number of mono- or polyunsaturated high molecular weight ketones. The preferred catalyst is a catalyst which is widely used in industry and which can be used for a long period without regeneration.

Side reactions, for example aldol condensation of the aldehyde, polymerization, the formation of byproducts or addition isomers by isomerization of the double bond, do not occur to an appreciable extent. The end product can generally be separated from the reaction mixture in a simple manner, for example by distillation, without the catalyst having to be separated previously. Special precautions to remove the end product formed from the reaction mixture rapidly are not necessary even in the production of very sensitive compounds and this has a favorable effect on the reliability and economy of the process.

The end products which can be prepared by the process of the invention are either solvents or valuable intermediates for the production of solvents, odorants, dyes, plastics and various natural substances. For example pseudo-ionone which can be prepared according to the invention is an important intermediate for the production of vitamin A and vitamin E. Many ketones such as methylheptadienone, farnesalacetone, anisalacetone and benzalacetone have aroused interest as perfumes.

The corresponding saturated ketones can be prepared from the unsaturated ketones by hydrogenation in the presence of palladium on activated carbon or Raney nickel as catalyst. Reference is made to the abovementioned publications and to Ullmanns Enzyklopaedie der technischen Chemie, volume 9, pages 544 et seq. as regards the use of the compounds.

The following Examples will further illustrate the process of the invention. The parts specified in the Examples, unless stated otherwise, are by weight. Parts by volume bear the same relation to parts by weight as the liter to the kilogram. In all the Examples the catalyst is used in the form of 4 mm pellets.

EXAMPLE 1

A mixture of 50 parts of 3,3-dimethylacrolein, 100 parts of acetone and 12 parts of zinc oxide is heated for 3 hours at 180° C and a pressure of 45 atmosphere in a vibrated autoclave. The reactor is then cooled and the mixture is fractionally distilled. 52.5 parts of 2-methyl-2,4-heptadien-6-one is obtained in a yield of 93% of theory based on 3,3-dimethylacrolein at a conversion 76% of theory and with a boiling point of 92° C at 15 mm Hg.

EXAMPLE 2

In the manner described in Example 1, a mixture of 50 parts of 3,3-dimethylacrolein and 100 parts of cyclohexanone is heated with 12 parts of zinc oxide for 4 hours at 180° C and a pressure of 50 atmospheres. After cooling and distilling the mixture, 70.5 parts of 2-(3′-methyl-2-butenylidene)-cyclohexanone is obtained in the boiling point range of from 93° to 96° C at 0.1 mm. The conversion is 81% of theory at a yield of 89% of theory (based on 3,3-dimethylacrolein).

EXAMPLE 3

50 Parts of 3,3-dimethylacrolein and 100 parts of acetophenone together with 10 parts of zinc oxide are kept for 3 hours at a temperature of 180° C under a pressure of 50 atmospheres. The reaction mixture is subjected to fractional distillation. 75.3 parts of 2-methyl-6-phenyl-2,4-hexadien-6-one (87% of theory based on 3,3-dimethylacrolein) is obtained at a conversion of 78% of theory. Boiling point: 107° to 110° C at $10^{116}$ 4 mm.

EXAMPLE 4

50 Parts of 3,3-dimethylacrolein and 100 parts of methyl ethyl ketone are reacted for 90 minutes with 10 parts of zinc oxide at 180° C and a pressure of 50 atmospheres in a vibrated autoclave. In the manner described in Example 1, 49.4 parts of 2-methyl-2,4-octadien-6-one having a boiling point of 106° C at 19 mm is obtained by working up the reaction mixture. The conversion is 68% of theory, the yield is 88% of theory based on 3,3-dimethylacrolein.

EXAMPLE 5

50 Parts of citral and 100 parts of acetone are reacted for 45 minutes at 200° C and a pressure of 80 atmospheres in the presence of 12 parts of a catalyst consisting of 12% by weight of copper(II) oxide and 88% by weight of zinc oxide. 45.6 parts of pseudoionone having a boiling point of 90° C at 0.01 mm is obtained analogously to Example 1. The conversion is 82% of theory and the yield based on citral is 88% of theory.

EXAMPLE 6

50 parts of crotonaldehyde and 100 parts of acetone are heated for half an hour at 140° and a pressure of 30 atmospheres with 15 parts of zinc oxide in an autoclave. 38.4 parts of 2,4-heptadien-6-one having a boiling point of 63° C at 10 mm is obtained analogously to Example 1 in a yield of 75% of theory based on crotonaldehyde at a conversion of 65% of theory.

EXAMPLE 7

60 Parts of isovaleraldehyde and 90 parts of acetone are heated with 15 parts of zinc oxide for 2 hours at 180° C and a pressure of 35 atmospheres. In the manner described in Example 1 56.4 parts of 2-methyl-4-hepten-6-one having a boiling point of 176° C at 750 mm is obtained. This is equivalent to a yield of 81% of theory based on isovaleraldehyde and a conversion of 73% of theory.

EXAMPLE 8

A mixture of 20 parts of acetaldehyde and 120 parts of acetone is heated with 14 parts of zinc oxide for 3 hours at 140° C and a pressure of 30 atmospheres. 28.7 Parts of 3-penten-2-one having a boiling point of 122° C at standard pressure is obtained by fractional distillation. The yield is 75% of theory based on acetaldehyde at a practically complete conversion of acetaldehyde.

EXAMPLE 9

60 Parts of benzaldehyde, 120 parts of acetone and 18 parts of zinc oxide are heated for 5 hours at 180° C and a pressure of 50 atmospheres. In the following fractional distillation 60.8 parts of crystalline benzalacetone is obtaine having a melting point of 42° C and a boiling point of 262° C at 760 mm. The yield is 92% of theory (based on benzaldehyde) at a conversion of 80% of theory.

EXAMPLE 10

A mixture of 50 parts of 3,3-dimethyl-acrolein and 120 parts of cyclopentanone has 17 parts of zinc oxide added to its and the whole is heated for 3 hours at 180° C and a pressure of 50 atmospheres. In the manner described in Example 9 there are obtained 63.5 parts of 2-(3'-methyl-2'-butenylidene)-cyclopentanone having a boiling point of 61° to 63° C at 0.01 mm in a yield of 90% of theory based on 3,3-dimethyl-acrolein at a conversion of 79% of theory.

EXAMPLE 11

100 Parts of methyl norbornyl ketone, 50 parts of 3,3-dimethyl-acrolein and 15 parts of zinc oxide are heated for 5 hours at 180° C and a pressure of 55 atmospheres. 85.7 Parts of (4-methyl-1,3-pentadienyl)-norbornyl ketone is obtained having a boiling point of 110° C at 0.01 mm analogously to Example 9. The yield is 88% of theory at a conversion of 80% of theory based on 3,3-dimethylacrolein.

EXAMPLE 12

100 Parts of methyl ethyl ketone, 50 parts of citral and 8 parts of zinc oxide are heated for 2 hours at 200° C and a pressure of 60 atmospheres. The reaction mixture is subjected to fractional distillation. 51.5 Parts of 7,11-dimethyl-4,6-10-dodecatrien-3-one is obtained having a boiling point of 105° to 108° C at 0.01 mm. The yield is 85% of theory at a conversion (based on citral) of 76% of theory.

EXAMPLE 13

100 Parts of methyl ethyl ketone, 50 parts of isovaleraldehyde and 10 parts of zinc oxide are heated for 5 hours at 160° C and a pressure of 40 atmospheres. 48 Parts of 7-methyl-4-octen-3-one (containing 3% by weight of 3,6-dimethyl-3-hepten-2-one) having a boiling point of 71° to 73° C at 10 mm is obtained analogously to Example 9. The yield of 7-methyl-4-octen-3-one is 80% of theory at a conversion of 71% of theory based on isovaleraldehyde.

EXAMPLE 14

40 Parts of propionaldehyde, 120 parts of acetone and 8 parts of zinc oxide are heated for 5 hours at 140° C and a pressure of 35 atmospheres. Fractional distillation of the reaction mixture gives 47.7 parts of 3-hexen-2-one having a boiling point of 140° C and 760 mm. The yield, at a conversion of 86%, is 82% of theory based on propionaldehyde.

EXAMPLE 15

50 Parts of anisaldehyde, 100 parts of acetone and 15 parts of zinc oxide are heated for half an hour at 200° C and a pressure of 60 atmospheres. 46.2 parts of 4-(p-methoxyphenyl)-3-buten-2-one is obtained analogously to Example 9 in the form of yellowish crystals having a melting point of 74° C and a boiling point of 109° to 110° C at 0.1 mm. The yield is 90% of theory (based on anisaldehyde) at a conversion of 79% of theory.

EXAMPLE 16

120 Parts of 2-methyl-1-hepten-6-one, 40 parts of 3,3-dimethyl-acrolein and 10 parts of zinc oxide are heated for 5 hours at 180° C and a pressure of 60 atmospheres. 63.5 Parts of 2,10-dimethyl-2,4,10-undecatrien-6-one having a boiling point of 120° to 123° C at 0.1 mm is obtained analogously to Example 9. The yield is 91% of theory (based on 3,3-dimethyl-acrolein) at a conversion of 78% of theory.

EXAMPLE 17

50 Parts of 1,1,5-trimethyl-2-formylcyclohexa-2,4-diene, 110 parts of acetone and 16 parts of zinc oxide are heated for 1 hour at 200° C and a pressure of 80 atmospheres. Analogously to Example 9, 33.6 parts of 4-(1',1',5'-trimethylcyclohexa-2',4'-dien-2'-yl)-3-buten-2-one having a boiling point of 93° to 94° C at 0.01 mm is obtained. The yield (based on 1,1,5-trimethyl-2-formyl-cyclohexa-2,4-diene) is 84% of theory; conversion is 63% of theory.

EXAMPLE 18

100 Parts of acetone, 60 parts of isobutyraldehyde and 8 parts of zinc oxide are heated for 3 hours at 160° C and a pressure of 35 atmospheres. 54.5 Parts of 5-methyl-3-hexen-2-one (isobutylideneacetone) having a boiling point of 155° C at 760 mm is obtained analogously to Example 9. The yield is 83% of theory (based on isobutyraldehyde) at a conversion of 70% of theory.

EXAMPLE 19

A mixture of 50 parts of 3,3-dimethyl-acrolein and 100 parts of mesityl oxide is heated in a vibrated autoclave having a capacity of 250 parts by volume with 12 parts of zinc oxide for 3 hours at 180° C and a pressure of 60 atmospheres, and then subjected to fractional distillation. 54.8 Parts of 2,8-dimethyl-2,5,7-nonatrien-4C having a boiling point of 82° c at 0.4 mm is obtained. The conversion is 72% and the yield (based on 3,3-dimethyl-acrolein) is 78% of theory.

EXAMPLE 20

A reaction mixture having the same composition as in Example 19 is heated with 12 parts of zinc oxide in the same reactor as in Example 1 for 5 hours at 160° C and a pressure of 45 atmmospheres and then worked up. 58.5 Parts of 2,8-dimethyl-2,5,7-nonatrien-4-one is obtained. The conversion is 68% and the yield is 88% of theory based on 3,3-dimethyl-acrolein.

EXAMPLE 21

100 Parts of 2-methyl-2,4-heptadien-6-one and 50 parts of 3,3-dimethyl-acrolein are heated with 10 parts of zinc oxide in an autoclave for 2 hours at 160° C and a pressure of 30 atmospheres. The reaction product is processed by distillation. 68.8 Parts of 2,10-dimethyl-2,4,7,9-undecatrien-6-one having a boiling point of 96° at $10^{116\ 4}$ mm is obtained in the form of yellow crystals. The yield (based on 3,3-dimethyl-acrolein) is 92% of theory and the conversion is 66%.

EXAMPLE 22

A mixture of 150 parts of β-ionone and 60 parts of 3,3-dimethyl-acrolein is stirred with 20 parts of zinc oxide in a round flask having a volume of 2000 parts by volume for 10 hours at atmospheric pressure and 145° C. Water formed by the condensation is immediately removed by supplying pentane into the vapor space above the reaction mixture. The reaction product is fractionated. 112 parts of 1-(2',6',6'-trimethyl-1'-cyclohexen-1'-yl)-7-methyl-1,4,6-octatrien-3-one is obtained having a boiling point of 120° to 122° C at $10^{116\ 4}$ mm. The yield is 93% of theory at a conversion of 65% based on 3,3-dimethyl-acrolein.

EXAMPLE 23

50 Parts of 3,3-dimethyl-acrolein and 100 parts of acetone are heated with 12 parts of a catalyst (which has been prepared by calcining a mixture of equimolar amounts of magnesium oxide, molybdenum dioxide and zinc oxide) for 3 hours at 180° C and a pressure of 30 atmospheres and the product is subjected to fractional distillation. 27 Parts of 2-methyl-2,4-heptadien-6-one is obtained which is equivalent to a yield of 43% of theory at a conversion of 86% based on 3,3-dimethyl-acrolein.

EXAMPLE 24

A mixture of 30 parts of isobutyraldehyde and 90 parts of acetone is heated with 12 parts of zinc oxide for 2 hours at 160° C and at a pressure of 45 atmospheres and then worked up. 27.5 parts of 5-methyl-3-hexen-2-one is obtained. The yield is 94% of theory at a conversion of 68% based on isobutyraldehyde.

EXAMPLE 25

310 Parts of farnesal is reacted with 1200 parts of acetone in an agitated autoclave having a capacity of 2000 parts by volume in the presence of 150 parts of zinc oxide for 5 hours at 180° C and a pressure of 30 atmospheres. The product is processed by distillation. 280 Parts of farnesalacetone having a boiling point of 128° to 130° C at $10^{116\ 4}$ mm is obtained. The yield is 93% of theory based on farnesal and the convesion is 88%.

EXAMPLE 26

A mixture of 150 parts of 2-methyl-1-hepten-6-one and 50 parts of citral is heated with 20 parts of zinc oxide in a round flask while stirring for 4 hours at 160° C and atmospheric pressure. Water thus formed is removed by distillation. The fractionation which follows gives 61 parts of 2,10,14-trimethylpentadeca-1,7,9,13-tetraen-6-one having a boiling point of 118° to 120° C at $10^{116\ 4}$ mm. The yield is 88% of theory based on citral, at a conversion of 81%.

We claim:
1. A process for the production of at least α,β-unsaturated ketones of the formula (I):

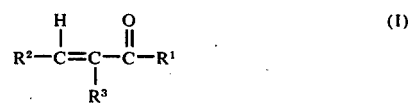

in which
R¹ and R² are branched or linear, saturated or unsaturated, aliphatic or cycloaliphatic-aliphatic hydrocarbon radicals of one to 20 carbon atoms or saturated or unsaturated cycloaliphatic hydrocarbon radicals of five to 12 carbon atoms which may also contain an alkyl group as a substituent and/or an endoalkylene group or an aralphatic hydrocarbon radical of seven to 15 carbon atoms or an aromatic hydrocarbon radical,
R³ is hydrogen or an aliphatic hydrocarbon radical of one to 10 carbon atoms and moreover R¹ and R³ together with the two adjacent carbon atoms may be common members of an alicyclic ring, by reaction of an aldehyde of the formula (II):

in which R² has the meanings given above with a ketone of the formula (III):

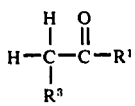

(III)

in which $R^1$ and $R^3$ have the meanings given above, in liquid phase wherein the reaction is carried out in the presence of a catalyst which consists essentially of zinc oxide.

2. A process as claimed in claim 1 in which $R^1$ and/or $R^2$ is a hydrocarbon radical of one to 16 carbon atoms.

3. A process as claimed in claim 1 wherein an aldedehyde of the formula (IIa):

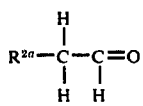

(IIa)

in which $R^{2a}$ has the meanings given in claim 1 for $R^2$ but contains one atom of carbon less is reacted with a ketone of formula (III).

4. A process as claimed in claim 1 wherein an aldehyde of the formula (IIb):

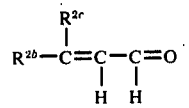

(IIb)

in which $R^{2b}$ has the meanings given in claim 1 for $R^2$ but contains from two to four carbon atoms less and $R^{2c}$ is methyl or ethyl is reacted with a ketone of formula (III).

5. A process as claimed in claim 1 wherein an aldehyde of formula (II) is reacted with an $\alpha,\beta$-unsaturated ketone.

6. A process as claimed in claim 1 wherein citral is reacted with acetone.

7. A process as claimed in claim 1 wherein dimethylacrolein is reacted with acetone.

8. A process as claimed in claim 1 carried out in the presence of a catalyst which is applied to a carrier material which is inert under the reaction conditions.

9. A process as claimed in claim 1 wherein said catalyst contains at least 80% of zinc oxide and from 0 to 20% of inert fillers.

* * * * *